United States Patent [19]
Bennett

[11] Patent Number: 5,231,986
[45] Date of Patent: Aug. 3, 1993

[54] METHOD AND SYSTEM FOR OPTIMIZING ACTIVITY THRESHOLD IN ACTIVITY BASED RATE ADAPTIVE PACEMAKERS

[75] Inventor: Tom D. Bennett, Shoreview, Minn.
[73] Assignee: Medtronic, Inc., Minneapolis, Minn.
[21] Appl. No.: 874,772
[22] Filed: Apr. 27, 1992
[51] Int. Cl.[5] .............................................. A61N 1/362
[52] U.S. Cl. .......................................... 607/11; 607/18
[58] Field of Search ................................... 128/419 PG

[56] References Cited

U.S. PATENT DOCUMENTS

| | | | |
|---|---|---|---|
| 5,040,534 | 8/1991 | Mann et al. | 128/419 PG |
| 5,065,759 | 11/1991 | Begemann et al. | 128/419 PG |

Primary Examiner—Kyle L. Howell
Assistant Examiner—Scott M. Getzow
Attorney, Agent, or Firm—Dwight N. Holmbo; Harold R. Patton

[57] ABSTRACT

A pacemaker capable of automatically adjusting the activity threshold setting of its activity sensor signal processing circuitry to its optimal value is disclosed. In one embodiment, the pacemaker maintains a running average of zero activity time and a cumulative summation of zero activity time over a predetermined history period. Periodically, the pacemaker computes a time difference between the running average of zero activity time and the cumulative summation of zero activity time, and adjusts the activity threshold of the activity sensor signal processing circuitry according to this computation. By basing the adjustment of activity threshold on a long-term average of zero activity time, the effects of cycle-to-cycle variation in sensed zero activity time are minimized. In another embodiment, the pacemaker periodically computes a time difference between a preprogrammed margin value and the cumulative summation of zero activity time. If the time difference is less than the predetermined margin, the activity threshold is increased. If the time difference is greater than the predetermined margin, the activity threshold is decreased.

8 Claims, 6 Drawing Sheets

METHOD AND SYSTEM FOR OPTIMIZING ACTIVITY THRESHOLD IN ACTIVITY BASED RATE ADAPTIVE PACEMAKERS

BACKGROUND OF THE INVENTION

The present invention generally relates to medical cardiac pacemakers and more specifically relates to a system and method for optimizing activity threshold in activity based rate adaptive cardiac pacemakers of the type which respond to the patient's metabolic demand and varies the pacing rate in accordance therewith.

Early cardiac pacemakers were asynchronous in operation, providing stimulating pulses to the heart at a fixed rate independent of the physiologic demand of the patient. In recent years, pacemakers which measure the metabolic demand for oxygen and vary the pacing rate in response thereto have become widely available. One modern method employed for measuring the need for oxygenated blood includes measurement of patient physical activity by means of an appropriate sensor. Generally, a rate responsive pacemaker which is responsive to patient physical activity includes a sensor which produces an output that varies between a maximum sensor output level and a minimum sensor output level and provides for a pacing rate which typically varies between a selectable lower pacing rate and an upper pacing rate. Such a pacemaker which utilizes a piezoelectric transducer, is disclosed in U.S. Pat. No. 4,485,813, issued to Anderson, et al., and assigned to Medtronic, Inc.

It has become common practice in recent years to provide programmable parameters in order to permit the physician to select and adjust the desired parameters to match or optimize the pacing system to the heart patient's physiologic requirements in an effort to minimize patient problems and to prolong or extend the useful life of an implanted pacemaker. Such systems are based upon utilizing a sensor derived variable that is an indicator of the patient's true metabolic and physiologic needs.

Activity based rate adaptive pacemakers typically have a programmable activity threshold parameter for adjusting the sensitivity of the circuitry to signals from the activity sensor. Historically, activity threshold parameters in activity based rate adpative pacemakers have been manually programmed and adjusted or optimized in an ad hoc iterative process. Often, because the process is difficult and lengthy, such parameters are not optimized, but left at nominal shipping values. Physicians using activity based rate adaptive pacemakers may have difficulty setting the activity threshold to an optimal setting since this parameter is device specific and there is a marked proliferation of activity based rate adaptive pacemakers by both Medtronic and other companies. Such a parameter will always tend to be device specific more than patient specific, so the physician has no inherent expertise in setting it optimally.

An activity based rate adaptive pacemaker which is capable of automatically and continuously determining and adjusting the activity threshold to an optimal setting would both significantly reduce programming time commitment by the physician and insure that activity threshold optimized at any single point in time will continue to remain optimal. One method for dealing with setting the activity threshold to an optimal setting for a given patient is disclosed in the auto set up idea disclosures included in U.S. patent application Ser. No. 07/567,372 entitled Rate Responsive Pacemaker and Method for Automatically Initializing the Same, filed in the name of Roline, et al., on Aug. 14, 1990, and assigned to Medtronic, Inc. The auto set up feature disclosed by Roline is desirable, but has limitations. It requires significant programming timing commitment by the physician. Also, it is unlikely that activity threshold optimized at any single point in time will remain optimal. The location of the pacemaker (subtle movements in the pocket), the IPG pocket characteristics, the patient's tissue composition (gaining/losing weight), the types of patient activities, and vibrational environmental factors may all impact how the activity threshold should be set. While Roline et al. constitutes an improvement over the conventional methods, it has not proven to be completely satisfactory in addressing and resolving the optimization problems associated with the optimization process.

It is an object of this invention to overcome the disadvantages and drawbacks of the prior art and to provide a method of activity-based rate-adaptive pacemaking which significantly reduces programming time commitment by the physician or repeated patient sessions in determining and adjusting the activity threshold to an optimal setting, and in which practice the activity threshold optimized at any single point in time will continue to remain optimal.

It is a further object of this invention to provide a system for practicing the above said method.

SUMMARY OF THE INVENTION

The present invention provides a method and system for continually and automatically optimizing and adjusting an activity threshold parameter which is directed to the problem of insuring that the activity threshold optimized at any single point in time will continue to remain optimal without further programming time commitment by a physician or repeated patient sessions. In the present invention, the pacemaker system includes a sensor implantable pacemaker and an external programmer. The system also includes means for continuously optimizing and automatically adjusting the activity threshold to its optimal value.

In the preferred embodiment, the process of automatically and continuously optimizing and readjusting an activity threshold parameter includes the steps of setting the activity threshold to an initial value and monitoring the average amount of time at rest in which there is an absence of activity counts. An activity count corresponds to an electrical event which exceeds the activity threshold of the activity sensor. Thereafter, the activity threshold is automatically adjusted to a lower value if the amount of time spent at zero counts is greater than the average amount of time spent at zero counts by more than a predetermined maximum difference value; otherwise, the activity threshold is automatically adjusted to a higher value if the amount of time spent at zero counts is less than the average amount of time spent at zero counts by more than a predetermined minimum difference value. In the preferred embodiment, the readjustment of activity threshold to a new optimized value would occur automatically every 24 hours. However, any time cycle may be used.

In another preferred embodiment, the activity threshold is automatically adjusted to a lower value if the amount of time spent at zero activity counts is greater than a predetermined maximum time value; otherwise, the activity threshold is automatically adjusted to a higher value if the amount of time spent at zero activity counts is less than a predetermined minimum time value.

BRIEF DESCRIPTION OF THE DRAWINGS

The above and other options, features and advantages of the present invention will become more apparent from the following more particular description thereof, presented in conjunction with accompanying drawings, wherein.

DETAILED DESCRIPTION OF THE PREFERRED EMBODIMENTS

Figure 1:
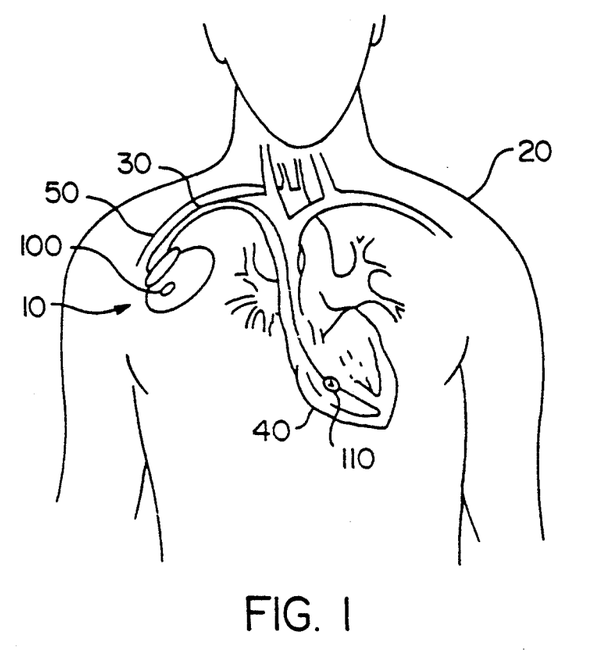
FIG. 1 is an illustration depicting how a pacemaker system in accordance with the present invention may be implanted in a patient.

FIG. 1 shows generally how a pacemaker 10 in accordance with the present invention may be implanted in a patient 20. A pacemaker lead 30 is electrically coupled to pacemaker 10 and extends into the patient's heart 40 via a vein 50. The distal end of lead 30 includes one or more exposed conductive electrodes 110 for receiving electrical pacing stimuli to the patient's heart 40.

Figure 2:
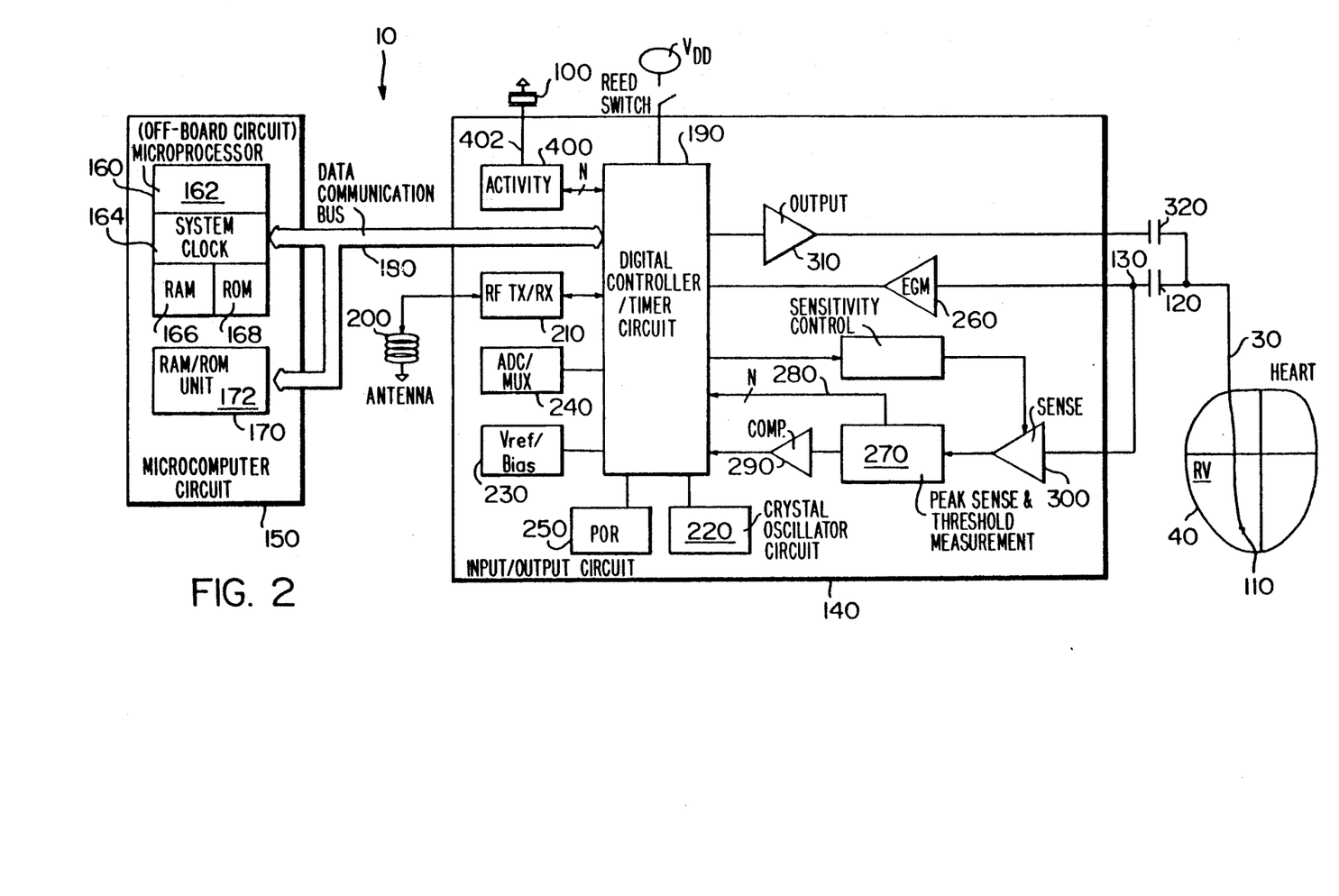
FIG. 2 is a block diagram representation of the circuitry of a pacemaker system to accomplish automatic activity threshold optimization adjustments according to the present invention.

Turning to FIG. 2, a block diagram of pacemaker 10 from FIG. 1 is shown. Although the present invention is described in conjunction with a pacemaker 10 having a microprocessor—based architecture, it will be understood that it could be implemented in any logic based, custom integrated circuit architecture, if desired. It will also be understood that the present invention may be utilized in conjunction with other implantable medical devices, such as cardioverters, defibrillators, neural stimulators, cardiac assist systems and the like.

In the embodiment shown in FIG. 1, pacemaker 10 includes an activity sensor 100, which may be, for example, a piezoelectric element bonded to the inside of the pacemaker's housing. Sensor 100 provides a sensor output which varies as a function of a measured parameter that relates to the metabolic requirements of patient 20.

Pacemaker 10 is schematically shown in FIG. 2 to be electrically coupled via a pacing lead 30 to a patient's heart 40. Lead 30 may be a transvenous endocardial electrode as shown or epicardial electrode (not shown), and can carry either unipolar or bipolar electrodes as is well known in the art. In the preferred embodiment, lead 30 includes an intracardiac electrode 110 located near its distal end and positioned within the right ventricular (RV) chamber of heart 40. In alternative embodiments, intracardiac electrode 110 may be positioned at other locations within the heart such as the left ventricular chamber or the atrium or both as in a dual chamber pacemaker. Electrode 110 is coupled through input capacitor 120 to node 130 and to input terminals of an input/output circuit 140.

Input/output circuit 140 contains the analog circuits for interface to the heart 40 and activity sensor 100, as well as for the application of stimulating pulses to heart 40 to control its rate as a function thereof under control of the software-implemented algorithms in a microcomputer circuit 150.

Microcomputer circuit 150 comprises an on-board circuit 160 and an off-board circuit 170. On-board circuit 160 includes a microprocessor 162, a system clock circuit 164, and on-board RAM 166 and ROM 168. Off-board circuit 170 includes an off-board RAM/ROM unit 172. Microcomputer circuit 150 is coupled by data communication bus 180 to a digital controller/timer circuit 190. Microcomputer circuit 150 may be fabricated of custom integrated circuit devices augmented by standard RAM/ROM components.

It will be understood that the electrical components represented in FIG. 2 are powered by an appropriate implantable battery power source, not shown, in accordance with common practice in the art.

An antenna 200 is connected to input/output circuit 140 for purposes of uplink/downlink telemetry through RF transmitter/receiver (RF TX/RX) unit 210. A crystal oscillator circuit 220 provides main timing clock signals to digital controller/timer circuit 190. A Vref/Bias circuit 230 generates stable voltage reference and bias currents for the analog circuits of input/output circuit 140. An analog-to-digital converter/multiplexor (ADC/MUX) unit 240 digitizes analog signals and voltages to provide "real-time" telemetry of intra cardiac signals and battery end-of-life (EOL) replacement function. A power-on-reset (POR) circuit 250 functions as a means to reset circuitry and related functions to a default condition upon detection of a low battery condition, which will occur for example upon initial device power-up or transiently in the presence of electromagnetic interference.

The operating commands for controlling the timing of pacemaker 10 are coupled by bus 180 to digital controller/timer circuit 190 wherein digital timers and counters are employed to establish the overall escape interval of the pacemaker, as well as various refractory, blanking and other timing windows for controlling the operation of the peripheral components within input/output circuit 140.

Digital controller/timer circuit 190 is coupled to a sense amplifier 300 and an electrogram amplifier 260 for receiving amplified and processed signals picked up from electrode 110 through lead conductor 30 and capacitor 120 representative of the electrical activity of the patient's heart 40. Sense amplifier 300 amplifies sensed electrical cardiac signals and provides this amplified signal to peak sense and threshold measurement circuitry 270, which provides an indication of peak sensed voltages and the measured sense amplifier threshold voltage on multiple conductor signal path 280 to digital controller/timer circuit 190. The amplified sense amplifier signal is also provided to a comparator 290. The electrogram signal developed by EGM amplifier 260 is used in those occasions when the implanted device is being interrogated by an external programmer, not shown, in order to transmit by uplink telemetry a representation of the analog electrogram of the patient's electrical heart activity as described in U.S. Pat. No. 4,556,063, issued to Thompson et al., assigned to the assignee of the present invention and incorporated herein by reference. An output pulse generator 310 provides the pacing stimulus to the patient's heart 40 through coupling capacitor 320 in response to a pacing trigger signal developed by digital controller/timer circuit 190 each time the escape interval times out, or an externally transmitted pacing command has been received, or in response to other stored commands as is well known in the prior art.

With continued reference to FIG. 2, input/output circuit 140 further includes sensitivity control circuitry 330 coupled between digital controller/timer circuit 190 and sense amplifier circuit 300. Sensitivity control circuit 330 controls the sense amplifier gain and thus the sensing threshold of sense amplifier 300 as instructed by digital controller/timer circuit 190. Digital controller/timer circuit 190 provides the appropriate information to microcomputer circuit 150 which determines whether the sensitivity threshold of sense amplifier 300 needs to be increased or decreased based on an analysis of sensed electrical cardiac signals.

Digital controller/timer circuit 190 is coupled to an activity circuit 400 for receiving, processing and amplifying signals received from activity sensor 100. Activity circuit 400 produces an activity signal which is representative of the patient's metabolic requirements and perpetually maintains the sensing threshold at which patient activity "counts" are recognized at an optimal level in accordance with the present invention. This activity threshold shall be hereinafter described in greater detail with reference to FIGS. 3, 4 and 5. As discussed above, the sensor 100 may take the form of a piezoelectric crystal mounted to the interior of the can of the pacemaker 10. Activity circuit 400 generates a signal or "count" each time the signal from the sensor 100 exceeds a certain optimal sensing threshold level. In prior art pacemakers of this general type, the threshold for the sensor 100 has typically been externally programmable to vary the amount of physical exertion required in order to trigger an output from the activity circuit 400. Alternatively, other sensors and sensor processing circuitry could be used in conjunction with the present invention so long as the sensor processing circuitry produces an output indicative of the patient's metabolic demand for oxygenated blood. The output from activity circuit 400 is supplied to the logic and timing circuitry of digital controller/timer circuit 190 for altering the escape interval. The details of the implementation of the escape interval alteration circuitry are not provided since they are believed to be within the skill of pacemaker designers.

Figure 3:
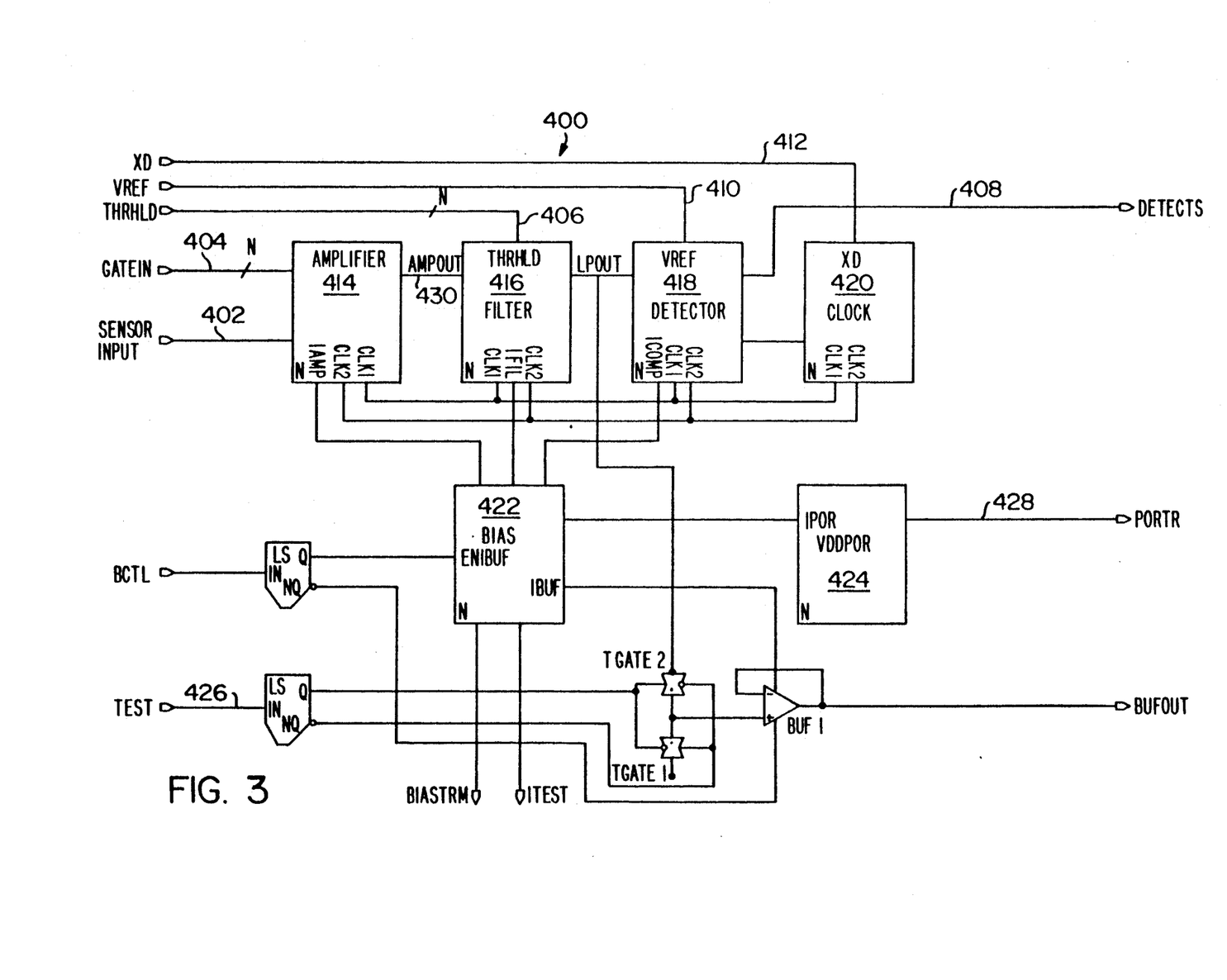
FIG. 3 is a block diagram representation of an activity sensing circuit to process activity sensor signals according to the present invention.

FIG. 3 is a functional block diagram of the activity circuit 400 illustrated in FIG. 2. This diagram illustrates the functional interface between the major circuit blocks in the activity circuit 400 and the inputs and outputs to the remainder of the pacemaker 10 circuitry. As stated above, other activity processing circuitry could be used with the present invention so long as the activity processing circuitry produces an output indicative of the patient's metabolic demand for oxygenated blood. In the embodiment disclosed in FIGS. 2 and 3, the sensor output from activity sensor 100 is applied to sensor input 402 of amplifier 414 depicted in FIG. 3. Amplifier 414 has a programmable gain via multiple conductor signal path 404, to compensate for variations in activity sensor 100 output which may occur until the build process has stabilized and is completely characterized. The output from amplifier 414 is cascaded via ampout line 430 to a low-pass filter 416. Filter 416 is an inverting, adjustable gain, offset-compensated, low-pass filter stage which drives a peak detector 418. The gain of filter 416 is a function of programmable activity threshold settings whereby activity threshold settings are adjusted via multiple conductor signal path 406 which interfaces directly with digital/controller timer circuit 190. Detector block 418 is a peak detector circuit with 100% hysteresis to discriminate against large spurious type inputs and to enhance detector 418 sensitivity to periodic input signals. Clock circuit 420 provides the timing necessary for amplifier 414, filter 416 and detector 418 to interface in synchrony with other sections of input/output circuit 140 and microcomputer circuit 150. Power for amplifier 414, filter 416, detector 418 and power-on-reset (VDDPOR) 424 blocks is provided by bias circuit block 422.

Figure 4:
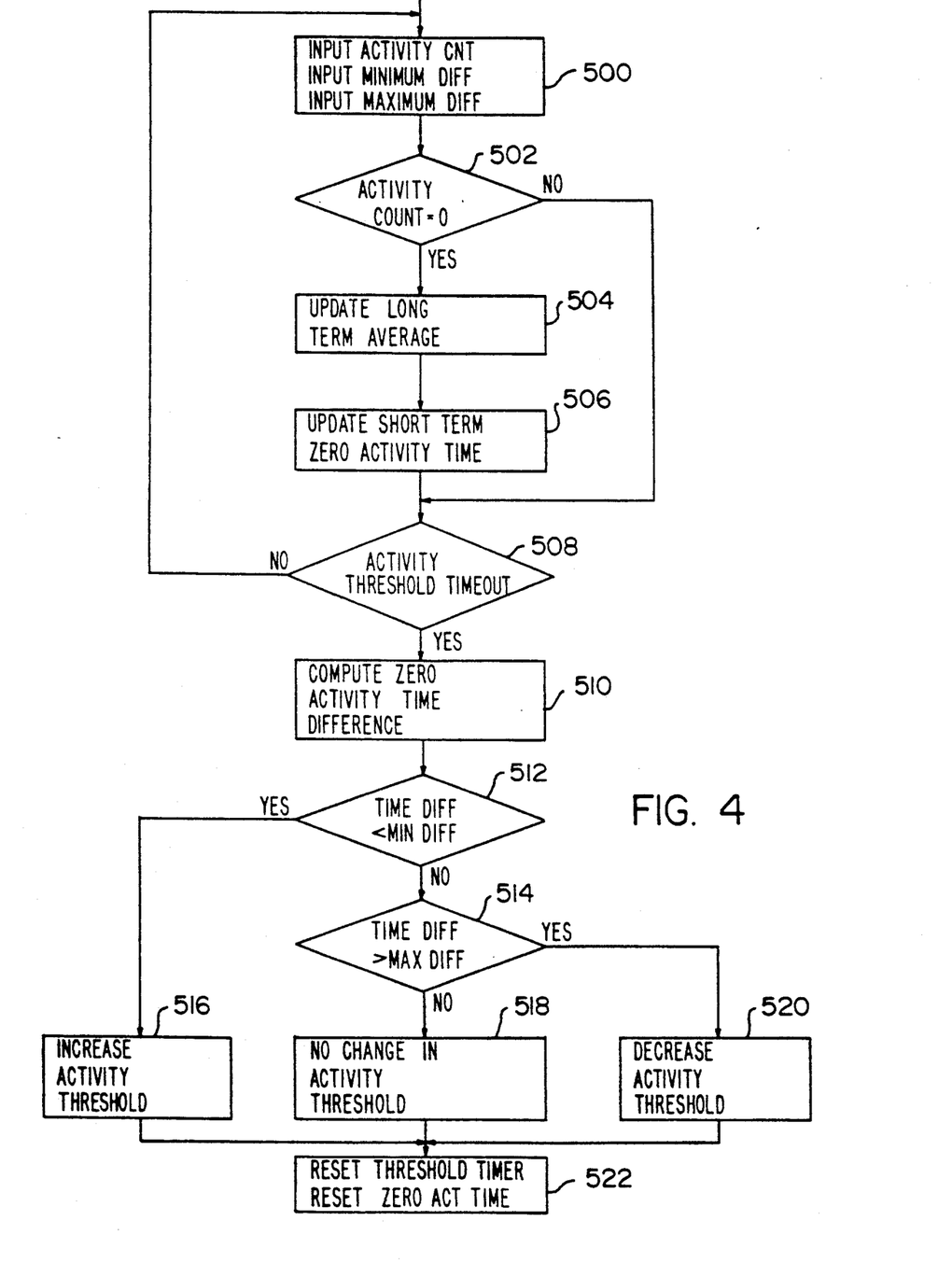
FIG. 4 is a simplified flowchart showing the basic function of the software of the pacemaker of FIG. 1 for continuously optimizing and automatically adjusting activity threshold using continuous updates of long term running average of zero activity time for purposes of deriving an optimized pacing rate.

Turning now to FIG. 4, a flow diagram is shown which illustrates an automatic activity threshold adjusting algorithm in accordance with the presently disclosed embodiment of the invention. The algorithm of FIG. 4 begins by manually programming predetermined minimum and maximum zero activity time differences where zero activity time difference is the last zero activity time measurement minus the zero activity long term time average, and upon automatically querying patient activity counts as represented by block 500. Upon querying patient activity, digital controller/timer circuit 190 automatically prompts microcomputer circuit 150 to calculate and update a long term average time in which there has been an absence of patient activity, as represented in block 502. It is also understood that an absolute value representative of long term average zero activity time as represented in block 502 could also be a ratio such as a percentage represented by comparing short term zero activity time with long term average zero activity time. Immediately following the update of long term average time of zero activity, microcomputer circuit 150 interrogates the most recent query of patient activity to determine if there has been an absence of patient activity. This interrogation is represented in decision block 504. Following each query of patient activity in which there is an absence of activity as indicated by zero activity counts, the microcomputer increments a value stored in RAM circuit 166 or RAM/ROM unit 172 which represents a total cumulative time in which there is an absence of patient activity as shown in block 506. If the most recent query indicates that patient activity has occurred due to the presence of activity counts, the total cumulative time representing zero patient activity is not incremented, and the algorithm repeats itself by continuing to query activity sensor 100 as represented in block 500. This process will continue until microcomputer 150 determines that an activity threshold timer time-out has occurred as represented in block 508.

As indicated above, in block 508 of FIG. 4, microcomputer 150 determines whether an activity threshold timer time-out has occurred. In the presently disclosed embodiment of the invention, it is contemplated that an activity threshold timer time-out will occur approximately every 24-hours, although time-out periods of any duration, ranging from one cardiac cycle to a month, may be employed.

Subsequent to an activity threshold timer time-out, microcomputer circuit 150 calculates a time difference as represented in block 510. This time difference is equal to the last updated total cumulative zero activity time previously calculated in block 506 minus the long term zero activity time average previously calculated in block 502. Next, in decision block 512, a determination by microcomputer circuit 150 is made whether the time difference computed by microcomputer circuit 150 in block 510 is less than the predetermined minimum zero activity time difference value manually programmed in block 500. If so, microcomputer circuit 150 automatically increases the activity threshold as shown in block 516, toward its optimal value by prompting digital/controller timer circuit 190 to adjust the threshold level of activity circuit 400 accordingly. Activity threshold adjustments for activity circuit 400 are accomplished by enabling different combinations of threshold setting inputs to filter 416 via multiple conductor signal path 406. This enabling function is performed by digital/controller timer circuit 190 setting the state of each conductor within multiple conductor signal path 406, high or low, at the direction of microcomputer circuit 150. When the activity threshold is increased, activity circuit 400 becomes less sensitive to signals received from activity sensor 100, and less activity sensor 100 signals are likely to exceed the threshold level.

If, however, the time difference value in block 510 exceeds the predetermined and manually programmed maximum zero activity time difference value in block 500 as represented in block 514, then the activity threshold level of activity circuit 400 is decreased toward its optimal value as represented in block 520. When the activity threshold is decreased, activity circuit 400 becomes more sensitive to signals received from activity sensor 100 and more activity sensor 100 signals are likely to exceed the threshold level.

If the time difference value in block 510 is not less than the predetermined minimum zero activity time difference value in block 500 or greater than the predetermined maximum zero activity time difference value in block 500 as represented by decision blocks 512 and 514 respectively, then the activity threshold level of activity circuit 400 is already at its optimal value and no adjustment of activity threshold level transpires as represented in block 518. Following any adjustment of the activity threshold level, or in the alternative, a decision to maintain the activity threshold level at its present value, microcomputer circuit 150 in conjunction with input/output circuit 140 resets the zero activity time value stored in RAM 166 or RAM/ROM 172 and the activity threshold timeout timer as represented in block 522. This process for automatically and continually adjusting the activity threshold level toward its optimal value is repeated in perpetuity without any further programming time commitment by a physician. Thus, activity threshold will remain optimal, independent of the location of the pacemaker which may change as a result of subtle movements in the pocket, the IPG pocket characteristics, the patient's tissue composition, or the types of patient activities and vibrational/environmental factors.

Figure 5:
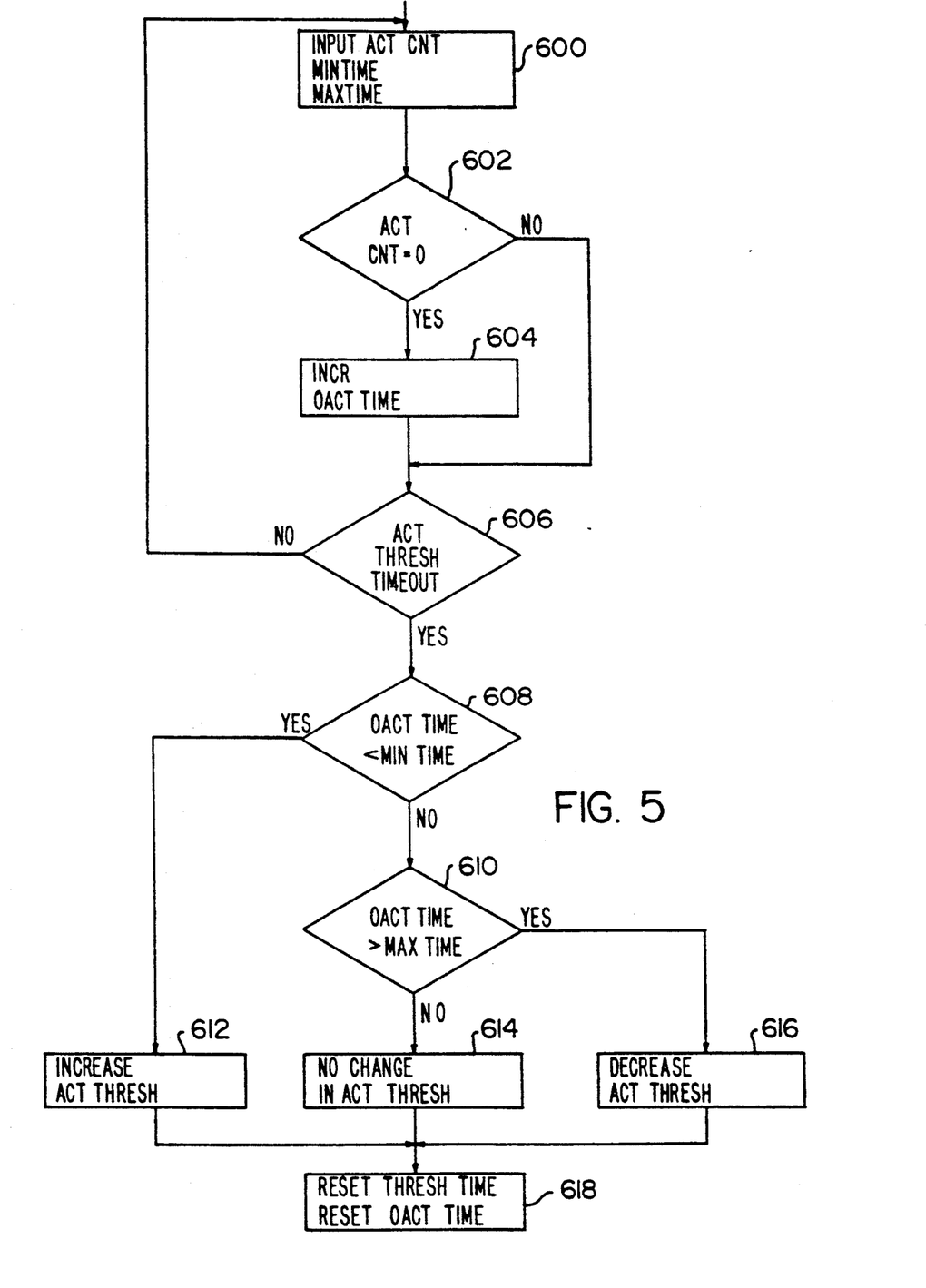
FIG. 5 is a simplified flowchart showing the basic function of the software of the pacemaker of FIG. 1 for continuously optimizing and automatically adjusting activity threshold using fixed targets for purposes of deriving an optimized pacing rate.

The algorithm depicted in FIG. 5 is an alternative embodiment, whereby steps 602 through 606 are carried out in the same manner as in the algorithm of FIG. 4. In this embodiment however, the algorithm begins by manually programming predetermined minimum and maximum time values, MINTIME and MAXTIME respectively, and also upon automatically querying patient activity counts as represented by block 600. From block 606, if an activity threshold timer time-out has not occurred, flow returns to block 600, as in the algorithm of FIG. 4. If an activity threshold time timeout has occurred, the comparison in block 608 is made, and the activity threshold is either increased, left the same, or decreased, as represented in blocks 612, 614 and 616 respectively. Thereafter, the activity threshold timer and zero activity time value are reset, as represented in block 618. The process for automatically and continually adjusting the activity threshold level toward its optimal value presented in this embodiment is analogous to the embodiment depicted in FIG. 4, whereby the optimization process repeats itself in perpetuity without any further programming time commitment by a physician.

Figure 6:
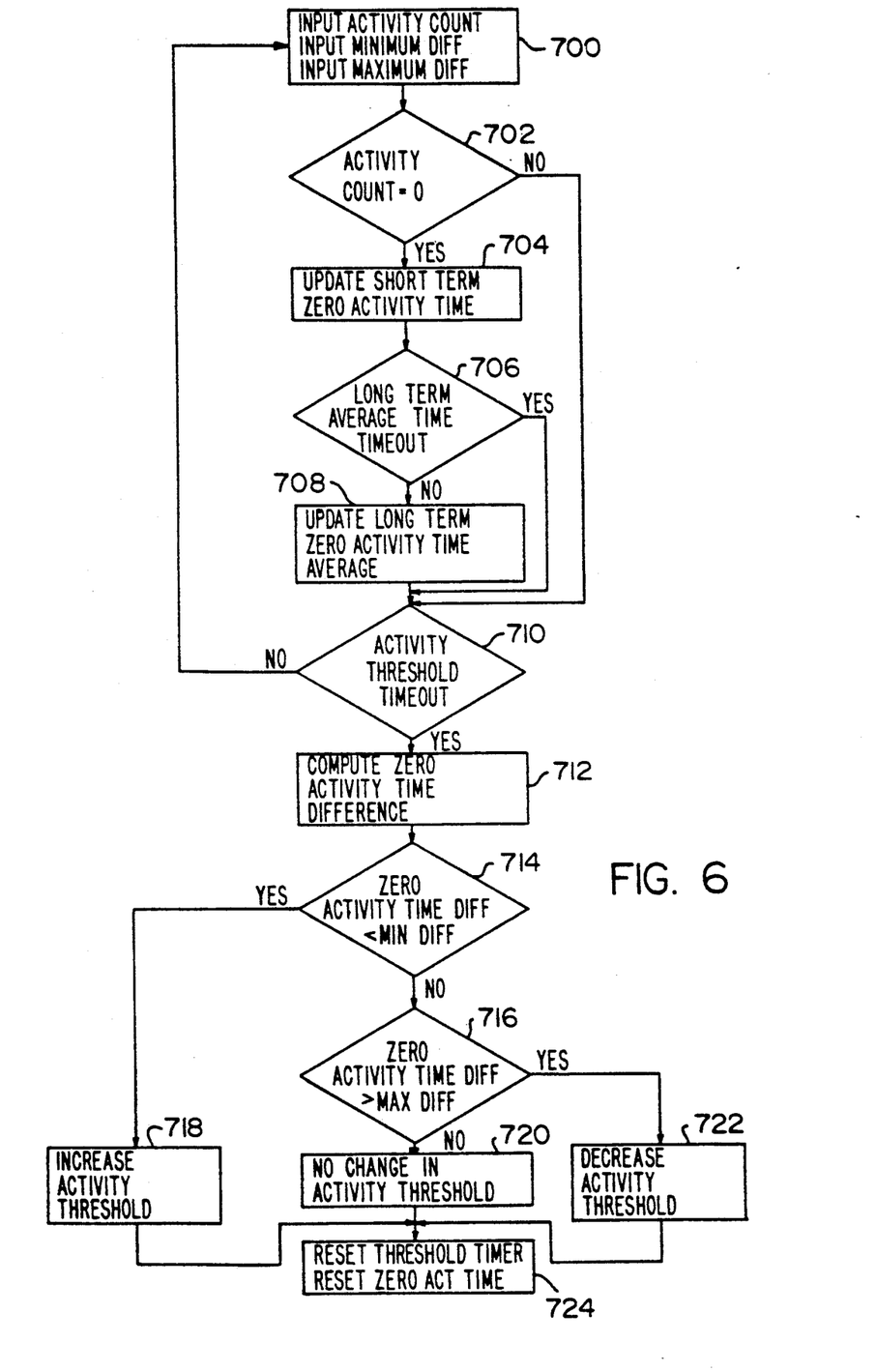
FIG. 6 is a simplified flowchart showing the basic function of the software of the pacemaker of FIG. 1 for continuously optimizing and automatically adjusting activity threshold using periodic updates of long term running average of zero activity time for purposes of deriving an optimized pacing rate.

FIG. 6 depicts another alternative embodiment, whereby the process for automatically and continually adjusting the activity threshold level toward its optimal value is analogous to the embodiment depicted in FIG. 4 with one exception. This embodiment periodically updates the absolute value of long term zero activity time average as illustrated by block 708, whenever an independent long term average timer times out in block 706, whereas the embodiment illustrated in FIG. 4 updates the absolute value of long term zero activity time average continuously.

From the foregoing detailed descriptions of particular embodiments of the invention, it should be apparent that a pacemaker has been disclosed which is provided with the capability of automatically adjusting the activity threshold of its activity sensing circuitry in order to minimize the probability of oversensing and undersensing on an on-going basis without requiring the attention of a physician. While particular embodiments of the present invention have been described herein in detail, it is to be understood that various alterations, modifications, and substitutions can be made therein without departing from the spirit and scope of the present invention, as defined in the claims, which follow. For example, it is contemplated by the inventors that timers and counters, such as those used for logging patient zero activity time and patient activity counts respectively, could be implemented by either software, hardware, or a combination of both.

I claim:

1. A pacemaker system for automatically optimitizing and adjusting an activity threshold parameter in a rate adaptive pacemaker, comprising:

optimizing means for automatically determining an optimal activity threshold value, said optimizing means including:
means for counting activity events;
means for monitoring a cumulative time spent during which no activity events are counted;
means for calculating and updating a long term average amount of time during which no activity events are counted;
means for comparing and updating a difference between said cumulative time spent in which no activity events are counted and said average amount of time during which no activity events are counted; means for automatically comparing said time difference with a predetermined minimum value; and adjusting means, responsive to said optimizing means, for automatically and periodically adjusting said activity threshold parameter to said optimal activity threshold value, said adjusting means including:
means for automatically and periodically increasing said activity threshold parameter, if said time difference is less than said minimum value.

2. The pacemaker system as defined in claim 1, wherein said optimizing means further includes means for automatically comparing said time difference with a predetermined maximum value.

3. The pacemaker system as defined in claim 2, wherein said adjusting means further includes means for automatically and periodically decreasing said activity threshold parameter, if said time difference is greater than said maximum value.

4. A pacemaker system for automatically optimizing and adjusting an activity threshold parameter in a rate adaptive pacemaker, comprising:
optimizing means for automatically determining an optimal activity theshold value, said optimizing means including:
means for counting activity events;
means for monitoring a cumulative time period during which no activity events are counted;
means for comparing said time period during which no activity events are counted with a preset minimum time value; and
adjusting means, responsive to said optimizing means, for automatically adjusting said activity threshold parameter to said optimal activity threshold value, said adjusting means including:
means for automatically increasing said activity threshold parameter, if said time period is less than said preset minimum time value.

5. The pacemaker system as defined in claim 4, wherein said optimizing means further includes means for comparing said time period with a preset maximum time value.

6. The pacemaker system as defined in claim 5, wherein said adjusting means further includes means for automatically decreasing said activity threshold parameter, if said time period is greater than said preset maximum time value.

7. A method for automatically optimizing and adjusting an activity threshold in activity based rate adaptive pacemakers, comprising the steps of:
initializing an activity count parameter;
initializing a minimum difference parameter;
initializing a maximum difference parameter;
initializing an activity threshold timeout parameter;
interrogating activity counts;
calculating a long term average time parameter representing an average amount of time during which there is an absence of said activity counts;
incrementing a cumulative time parameter if most recent interrogation of said activity counts indicates zero counts;
calculating a difference between last updated said long term average time parameter and last updated said cumulative time parameter, if said activity threshold timeout parameter has reached a value set during initialization;
decreasing said activity threshold, if said difference exceeds said maximum difference parameter; and
increasing said activity threshold, if said difference is less than said minimum difference parameter.

8. A method for automatically optimizing and adjusting an activity threshold in activity based rate adaptive pacemakers, comprising the steps of:
initializing an activity count parameter;
initializing a minimum time parameter;
initializing a maximum time parameter;
initializing an activity threshold timeout parameter;
interrogating activity counts;
incrementing a cumulative time parameter if most recent interrogation of said activity counts indicates zero counts;
comparing said cumulative time parameter with said minimum time parameter, if said activity threshold timeout parameter has reached a value set during initialization;
increasing said activity threshold, if said cumulative time parameter is less than said minimum time parameter;
comparing said cumulative time parameter with said maximum time parameter, if said cumulative time parameter is not less than said minimum time parameter; and
decreasing said activity threshold, if said cumulative time parameter exceeds said maximum time parameter.

* * * * *